(12) United States Patent
Bernardi

(10) Patent No.: US 6,758,815 B2
(45) Date of Patent: Jul. 6, 2004

(54) APPARATUS AND METHOD FOR INDICATING MECHANICAL STIFFNESS PROPERTIES OF BODY TISSUE

(76) Inventor: Richard Bruce Bernardi, 440 Woodcrest Rd., Wayne, PA (US) 19087

( * ) Notice: Subject to any disclaimer, the term of this patent is extended or adjusted under 35 U.S.C. 154(b) by 0 days.

(21) Appl. No.: 09/978,876

(22) Filed: Oct. 17, 2001

(65) Prior Publication Data

US 2003/0073905 A1 Apr. 17, 2003

(51) Int. Cl.[7] .............................................. A61B 8/00
(52) U.S. Cl. ....................................... 600/437; 600/442
(58) Field of Search ................................ 600/437, 587, 600/442, 443, 449

(56) References Cited

U.S. PATENT DOCUMENTS

| | | | | |
|---|---|---|---|---|
| 4,664,123 A | * | 5/1987 | Iinuma | 600/443 |
| 5,107,837 A | * | 4/1992 | Ophir et al. | 600/437 |
| 5,462,058 A | * | 10/1995 | Yamada et al. | 600/454 |
| 5,810,731 A | * | 9/1998 | Sarvazyan et al. | 600/438 |
| 5,831,168 A | * | 11/1998 | Shinomura et al. | 73/602 |
| 6,039,691 A | * | 3/2000 | Walker et al. | 600/452 |
| 6,068,597 A | * | 5/2000 | Lin | 600/443 |
| 6,099,471 A | * | 8/2000 | Torp et al. | 600/438 |
| 6,352,507 B1 | * | 3/2002 | Torp et al. | 600/438 |
| 6,371,912 B1 | * | 4/2002 | Nightingale et al. | 600/437 |
| 6,517,485 B2 | * | 2/2003 | Olstad et al. | 600/438 |
| 2002/0095087 A1 | * | 7/2002 | Mourad et al. | 600/442 |

OTHER PUBLICATIONS

"Investigation of Real–time Remote Palpation Imaging", Kathryn R. Nightingale, Medical Imaging 2001, Proceedings of SPIE vol. 4352 (2001), pp. 113–119.

International Search Report of PCT/US02/33043 dated Mar. 7, 2003.

* cited by examiner

*Primary Examiner*—Shawna Jeannine Shaw
(74) *Attorney, Agent, or Firm*—RatnerPrestia

(57) ABSTRACT

Apparatus and method for indicating mechanical stiffness properties of body tissue employing Doppler imaging techniques. Ultrasonic signals that are transmitted to the target not only are reflected for developing images of the target from the reflections, but, by appropriate selection of the intensity of the transmitted signals, the body tissue being investigated is deformed or moved when the transmitted signals impinge on the target. The deformation or movement of the body tissue being investigated is imaged and is representative of the mechanical stiffness of this body tissue.

7 Claims, 2 Drawing Sheets

APPARATUS AND METHOD FOR INDICATING MECHANICAL STIFFNESS PROPERTIES OF BODY TISSUE

TECHNICAL FIELD

The present invention relates, in general, to examining body parts and, in particular, to an apparatus and method by which the mechanical stiffness of body tissue being investigated is determined from ultrasonic transmissions to and reflections from the body tissue.

BACKGROUND OF THE INVENTION

At the present time, ultrasonic imaging is the second largest medical imaging modality after X-ray imaging. In ultrasonic imaging, images are formed by transmitting high frequency acoustic waves into the body and then appropriately mapping the response of returning echoes as the original acoustic signal propagates into the body. An acoustic echo is generated at each interface within the body, which is characterized by an impedance discontinuity. Typically, an image is obtained by mapping the intensity of the returning echo signals as a function of range and direction of propagation. Movement of the ultrasonic waves within a plane allows one to analyze sequentially tissue responses from a large number of directions. Images developed in this manner are known as B-mode images (i.e., "body" mode images).

Other ultrasonic imaging techniques are in practice at the present time. Color Doppler mode is one such other technique. Color Doppler mode is a methodology in which the mean Doppler frequency shift imposed upon the returning acoustic echoes by moving target structures, such as the blood, is measured and mapped. The mean Doppler shift is determined by measuring the mean phase rotation or time delay between successive acoustic pulses in a series of pulses known as a packet. Likewise, Power Doppler is a mode in which the intensity of the Doppler signal, rather than the mean frequency shift, is mapped to form an image.

Recently, an imaging mode, known as harmonic imaging, has been introduced. In this method, an ultrasonic pulse is transmitted into the body as with conventional B-mode imaging. Instead of sensing the return of acoustic echoes at the same frequency as the original pulses, filtering techniques are used to sense signals at harmonic frequencies. The intensity of these sensed signals is then mapped in a conventional manner. Because these signals are generated as a function of the non-linear propagation characteristics of the tissue, different anatomical features can be observed; perhaps with better contrast In a recently published paper entitled "Investigation of Real-time Remote Palpation Imaging" by Nightingale, Soo, Nightingale, Palmeri and Trahey, *Proceedings SPIE Medical Imaging* 2001, there is described an experiment in which tissue was first insonified with a conventional ultrasonic pulse and the radio frequency signal associated with the returning acoustic echo then was recorded. Next, the tissue was insonified with a continuous (i.e., relatively long) acoustic wave (120–300 W/cm$^2$) that generated a force within the tissue. Then, the displacement of the tissue resulting from this force was measured using a radio frequency cross-correlation technique between the initial ultrasonic pulse and a second ultrasonic pulse. A displacement, from the resultant force, of as much as 30 microns could be observed. Maximum displacements were generally obtained within 5 ms. The tissue displacements correlated well with B-mode image anatomical structures. The amount of displacement and the recovery time can be associated with the stiffness properties of the propagation media.

This displacement phenomenon can be explained in terms of the physics of wave propagation. When a wave travels in a medium, be it an acoustic wave or an electromagnetic wave, it carries with it not only energy (E) but also momentum (P). As the acoustic wave propagates into tissue, however, energy is absorbed due to inelastic transport processes. Associated with this energy loss is a commensurate change in momentum. Momentum changes also can occur when energy is reflected from acoustic interfaces. This may be an elastic process.

From Newton's Laws, this momentum change imposes a force on the differential tissue volume in the path of propagation (dP/dt=F). This force, in turn, causes the infinitesimal tissue volume to move, F=mass×acceleration. The extent of the movement is a function of the stiffness of the material as well as the local absorption.

SUMMARY OF THE INVENTION

In its simplest form, the present invention may employ algorithms and hardware similar to those that have been used previously in Doppler imaging to display images of the movement of body parts. In the present invention, the ultrasonic signals that are transmitted to the target not only are reflected for developing images of the target from the reflections, but, by appropriate selection of the intensity of the transmitted signals, the body tissue being investigated is deformed or moved when the transmitted signals impinge on the target to measure the displacement due to ultrasonic wave propagation. The deformation or movement of the body tissue being investigated is imaged and is representative of the mechanical stiffness of this body tissue.

Apparatus for indicating mechanical stiffness properties of body tissue, constructed in accordance with the present invention, includes transmitter means for transmitting to a target in a body (a) a first ultrasonic pulse having a first acoustic intensity sufficient to deform the target, and (b) subsequently a second ultrasonic pulse having a second acoustic intensity, different from the acoustic the intensity of the first ultrasonic pulse, sufficient to deform the target. This apparatus also includes receiver means for receiving (a) a reflection from the target of the first ultrasonic pulse and developing a first signal representative of the position after deformation of the target caused by the first ultrasonic pulse, and (b) subsequently a reflection from the target of the second ultrasonic pulse and developing a second signal representative of the position after deformation of the target caused by the second ultrasonic pulse. This apparatus further includes indicating means responsive to the first signal and the second signal for indicating the change of deformation of the target caused by the second ultrasonic pulse relative to the deformation of the target caused by the first ultrasonic pulse.

A method for indicating mechanical stiffness properties of body tissue according to the present invention includes the steps of transmitting to a target in a body a first ultrasonic pulse having a first acoustic intensity sufficient to deform the target, receiving a first reflection from the target of the first ultrasonic pulse, transmitting a second ultrasonic pulse having a second acoustic intensity, different from the acoustic intensity of the first ultrasonic pulse, sufficient to deform the target, and receiving a second reflection from the target of the second ultrasonic pulse. This method also includes the steps of developing from the first reflection a first indication of deformation of the target caused by the first ultrasonic pulse, developing from the second reflection a second indication of deformation of the target caused by the second ultrasonic pulse, and developing from the first deformation indication and the second deformation indication an indication of the deformation of the target caused by the second ultrasonic pulse relative to the deformation of the target caused by the first ultrasonic pulse.

It is to be understood that the foregoing general description of the present invention and the following detailed description of the present invention are exemplary, but are not restrictive of the invention.

BRIEF DESCRIPTION OF THE DRAWINGS

The present invention is best understood from the following detailed description when read in connection with the accompanying drawings.

DETAILED DESCRIPTION OF THE INVENTION

Figure 1:
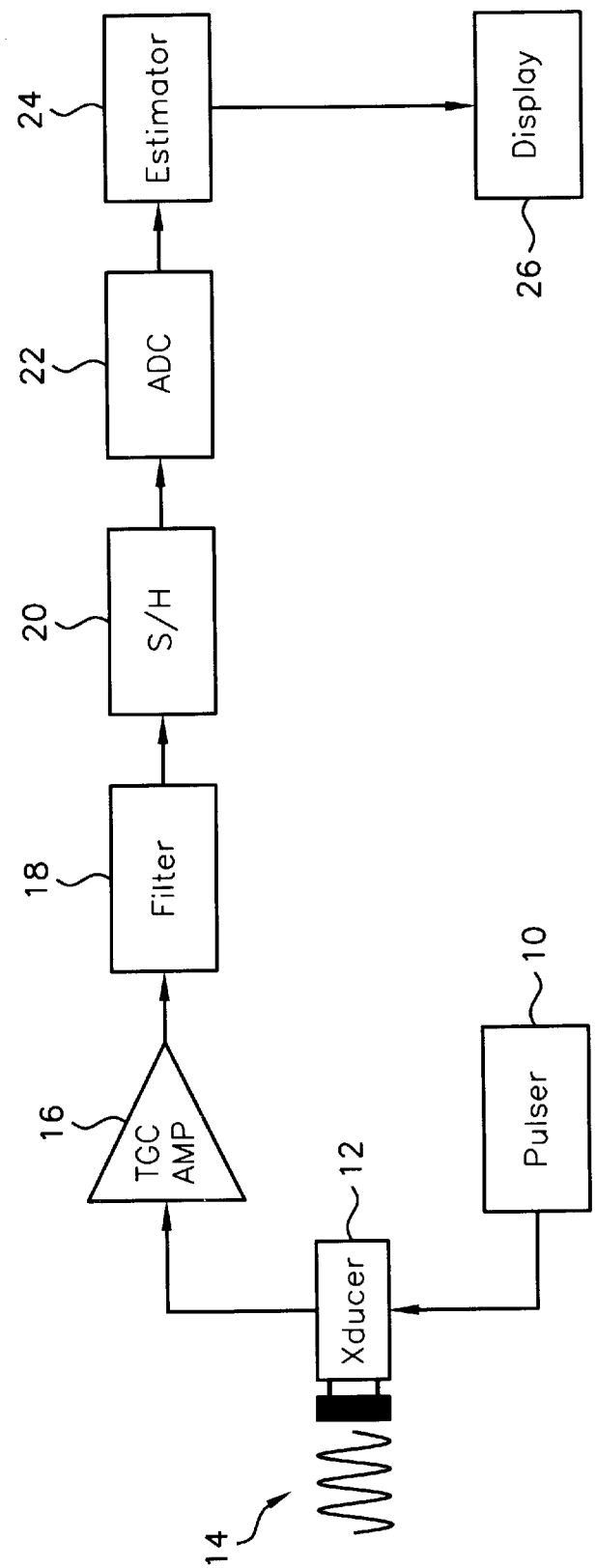
FIG. 1 is a block diagram of a first embodiment of apparatus for indicating mechanical stiffness properties of body tissue constructed in accordance with the present invention.

Referring to FIG. 1, a first embodiment of apparatus for indicating mechanical stiffness properties of body tissue, constructed in accordance with the present invention, includes transmitter means for transmitting to a target in a body a first ultrasonic pulse having a first acoustic intensity sufficient to deform the target and subsequently a second ultrasonic pulse having a second acoustic intensity, different from the acoustic intensity of the first ultrasonic pulse, sufficient to deform the target. For the FIG. 1 embodiment of the present invention, such transmitting means include a pulser 10 and a transducer 12. Pulser 10 serves as the source of energy for the ultrasonic pulses that are conducted to transducer 12 and, in turn, are transmitted to a target in a body as represented by the acoustic waveform 14.

It will be understood that the present invention may involve transmitting more than two ultrasonic pulses. Rather, a series of ultrasonic pulses may be transmitted and any two of the series are considered a transmitted first ultrasonic pulse and a transmitted second ultrasonic pulse.

In accordance with the present invention, as will be understood from the explanation provided below, to determine the relative deformations of the target caused by deformation of the target by the transmitted first ultrasonic pulse and the deformation of the target by the transmitted second ultrasonic pulse (i.e., two consecutive transmitted ultrasonic pulses), the acoustic intensities of the consecutive transmitted ultrasonic pulses are different. This can be accomplished by setting the acoustic intensity of the transmitted second ultrasonic pulse either greater or less than the acoustic intensity of the transmitted first ultrasonic pulse with only two different levels of acoustic intensity or with three or more levels of acoustic intensity.

The FIG. 1 apparatus for indicating mechanical stiffness properties of body tissue, constructed in accordance with the present invention, also includes receiver means for receiving a reflection from the target of the first ultrasonic pulse and developing a first signal representative of the position after deformation of the target caused by the first ultrasonic pulse and subsequently a reflection from the target of the second ultrasonic pulse and developing a second signal representative of the position after deformation of the target caused by the second ultrasonic pulse. Waveform 14 also represents reflections of the ultrasonic signals from the target. For the FIG. 1 embodiment of the present invention, such receiving means include transducer 12. The reflections from the target of the transmitted first and second ultrasonic pulses, respectively, are converted to electrical signals by transducer 12.

The electrical signals developed by transducer 12 from the reflections from the target of the transmitted first and second ultrasonic pulses are low level and are amplified, as shown by the FIG. 1 embodiment of the present invention, by a time gain compensation amplifier 16. Because energy is absorbed as the ultrasonic pulses propagate through tissue, the gain of time gain compensation amplifier 16 is increased with time corresponding to the increased depth within the body from which the reflections return. This equalizes the returning electrical signal amplitude to make the signals relatively independent of the depth within the body from which the reflections return.

As shown by FIG. 1, the amplified signal for each reflection then is filtered by a bandpass filter 18 to remove unwanted electrical signals outside the frequency range of the returning reflections. This improves the signal to noise ratio.

In the FIG. 1 embodiment of the present invention, the signals representative of the received reflections of the first and second ultrasonic pulses, respectively, that are transmitted by transducer 12 then pass to a sample and hold circuit that retains the signal voltage at a given instant in time. This voltage is converted from an analog signal to a digital signal by an analog-to-digital converter 22. Sequences of digital signals, developed by analog-to-digital converter 22, are representative of the received reflections of the first and second ultrasonic pulses, respectively, that are transmitted by transducer 12. The sampling by sample and hold circuit 20 is performed sufficiently rapidly in time (at or exceeding the Nyquist rate) to record, in digital form, the information contained in the original analog signals developed from the reflections of the transmitted first and second ultrasonic pulses. It should be noted that modern analog to digital converters might not require the inclusion of a sample and hold circuit.

The FIG. 1 apparatus for indicating mechanical stiffness properties of body tissue, constructed in accordance with the present invention, further includes indicating means responsive to the first signal representative of the position of the target after deformation of the target caused by the transmitted first ultrasonic pulse and the second signal representative of the position of the target after deformation of the target caused by the transmitted second ultrasonic pulse for indicating the change of deformation of the target caused by the transmitted second ultrasonic pulse relative to the deformation of the target caused by the transmitted first ultrasonic pulse. For the FIG. 1 embodiment of the present invention, such indicating means include means for shifting a selected segment of the waveform of one of the two signals representative of the positions of the target after deformation of the target caused by the transmitted first ultrasonic pulse or the transmitted second ultrasonic pulse till maximum coincidence is achieved between the selected segment with the corresponding segment of the waveform of the other signal.

In particular, for the FIG. 1 embodiment of the present invention, an estimator 24 includes circuitry which first stores the digital signal representative of the reflection of the first ultrasonic pulse transmitted by transducer 12 and the digital signal representative of the reflection of the second ultrasonic pulse transmitted by transducer 12 (i.e., digital signals representative of reflections of consecutive transmitted ultrasonic pulses). The circuitry of estimator 24 then chooses a short segment of the waveform of the reflection of the transmitted first ultrasonic pulse, perhaps 8 to 32 samples long, starting at the beginning of the waveform, and compares this to the corresponding segment of the waveform of the reflection of the transmitted second ultrasonic pulse. Because slight movement of the position of the target is anticipated, estimator 24 chooses segments of the waveforms in the vicinity of the expected position until a maximum match is achieved. Mathematically, this is known as a cross-correlation and FIG. 1 embodiment of the present invention may be characterized as the cross-correlation embodiment. It should noted that the gain of the digital signals representative of the reflections is adjusted to compensate for the differences in the acoustic intensities of the transmitted ultrasonic pulses prior to performing the cross-correlation operation.

The difference in signal location, namely the extent of movement from the starting point of the waveform segment to the point that produces the maximum waveform correlation, corresponds to the displacement of the target that has resulted for that segment. This delay or shift then is recorded. The process is repeated for each succeeding segment of the waveform of the reflection of the first ultrasonic pulse transmitted by transducer 12 with each succeeding segment compared via cross-correlation with the corresponding segment of the waveform of the reflection of the second ultrasonic pulse transmitted by transducer 12.

In this way, estimator 24 develops a signal representative of the relative shift in the selected segments of the waveforms to achieve maximum coincidence of the selected segments of the waveforms. This signal drives a display 26 of the indicating means to present the image of the target and the deformation of the target. In particular, the amplitude of the signal developed by estimator 24 is obtained as an average of the first signal developed from the reflection of the first ultrasonic pulse transmitted by transducer 12 and the second signal developed from the reflection of the second ultrasonic pulse transmitted by transducer 12 and is used to provide a conventional ultrasonic B-mode image. Similarly, the shift in magnitude is used to develop a deformation image indicative of stiffness. Because the force differential between the first ultrasonic pulse transmitted by transducer 12 and the second ultrasonic pulse transmitted by transducer 12 is linearly related to the difference in acoustic intensities between the two transmitted pulses, the actual stiffness measurement is adjusted to compensate for the fact that the magnitude of the force difference decreases as the pulses travel through the tissue due to acoustic energy absorption.

It should be noted that the signal developed by estimator 24, that is representative of the relative shift in the selected segments of the waveforms to achieve maximum coincidence of the selected segments of the waveforms, also can drive a meter that indicates, in either analog or digital form, the deformation of the target.

Figure 2:
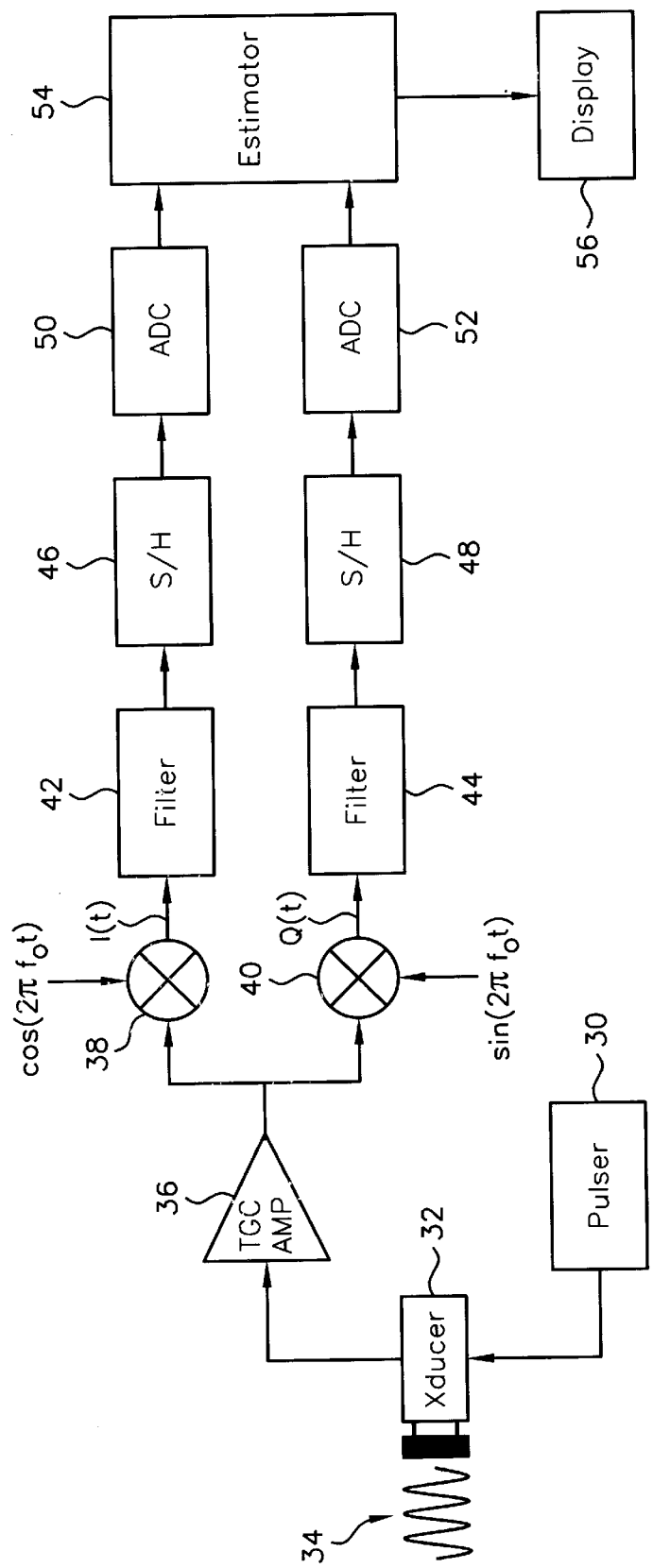
FIG. 2 is a block diagram of a second embodiment of apparatus for indicating mechanical stiffness properties of body tissue constructed in accordance with the present invention.

Referring to FIG. 2, a second embodiment of apparatus for indicating mechanical stiffness properties of body tissue, constructed in accordance with the present invention, includes transmitter means for transmitting to a target in a body a first ultrasonic pulse having a first acoustic intensity sufficient to deform the target and subsequently a second ultrasonic pulse having a second acoustic intensity, different from the acoustic intensity of the first ultrasonic pulse, sufficient to deform the target. For the FIG. 2 embodiment of the present invention, such transmitting means include a pulser 30 and a transducer 32. Pulser 30 serves as the source of energy for the ultrasonic pulses that are conducted to transducer 32 and, in turn, are transmitted to a target in a body as represented by the waveform 34.

As with the FIG. 1 embodiment of the present invention, more than two ultrasonic pulses may be transmitted by transducer 32. Preferably, a series of ultrasonic pulses are transmitted and any two of the series are considered a transmitted first ultrasonic pulse and a transmitted second ultrasonic pulse.

As with the FIG. 1 embodiment of the present invention, to determine the relative deformations of the target caused by deformation of the target by the transmitted first ultrasonic pulse and the deformation of the target by the transmitted second ultrasonic pulse (i.e., two consecutive transmitted ultrasonic pulses), the acoustic intensities of the consecutive transmitted ultrasonic pulses are different. This can be accomplished by setting the acoustic intensity of the transmitted second ultrasonic pulse either greater or less than the acoustic intensity of the transmitted first ultrasonic pulse with only two different levels of acoustic intensity or with three or more levels of acoustic intensity.

The FIG. 2 apparatus for indicating mechanical stiffness properties of body tissue, constructed in accordance with the present invention, also includes receiver means for receiving a reflection from the target of the first ultrasonic pulse and developing a first signal representative of the position after deformation of the target caused by the first ultrasonic pulse and subsequently a reflection from the target of the second ultrasonic pulse and developing a second signal representative of the position after deformation of the target caused by the second ultrasonic pulse. Waveform 34 also represents reflections of the ultrasonic signals from the target. For the FIG. 2 embodiment of the present invention, such receiving means include transducer 32. The reflections from the target of the transmitted first and second ultrasonic pulses, respectively, are converted to electrical signals by the transducer 32.

The electrical signals developed by transducer 32 from the reflections from the target of the transmitted first and second ultrasonic pulses are low level and are amplified, as shown by the FIG. 2 embodiment of the present invention, by a time gain compensation amplifier 36. Because energy is absorbed as the ultrasonic pulses propagate through tissue, the gain of time compensation gain amplifier 36 is increased with time corresponding to the increased depth within the body from which the reflections return. This equalizes the returning electrical signal amplitude to make the signals relatively independent of the depth within the body from which the reflections return.

As shown by FIG. 2, the amplified signal then is divided and the components of the divided signal individually enter mixers 38 and 40. Mixers 38 and 40 convert the radio frequency waveform, representative of the original returning reflections, into two baseband signals that are in phase with the quadrature reference signals $\cos(2\pi f_o t)$ and $\sin(2\pi f_o t)$ of the mixers. These in-phase and quadrature signals are designated as I(t) and Q(t).

For the FIG. 2 embodiment of the present invention, each of the in-phase and quadrature signals individually passes through a filter 42 and 44 to remove unwanted electrical signals outside the frequency range of the returning reflections. This improves the signal to noise ratio.

In the FIG. 2 embodiment of the present invention, the in-phase and quadrature signals then pass individually to sample and hold circuits 46 and 48 that retain the signal voltages at a given instant in time. These voltages are separately converted from analog signals to digital signals by analog-to-digital converters 50 and 52. Sequences of the I(t) and Q(t) digital signals, developed by analog-to-digital converters 50 and 52, are representative of the received reflections of the first and second ultrasonic pulses, respectively, that are transmitted by transducer 32. The sampling by sample and hold circuits 46 and 48 is performed sufficiently rapidly (at or exceeding the Nyquist rate) to record, in digital form, the information contained in the original analog signals developed from the reflections of the transmitted first and second ultrasonic pulses. These sequences are designated as $$I_1(n)Q_1(n) \text{ and } I_2(n)Q_2(n)$$

where:
the subscripts refer to the transmitted first ultrasonic pulse and the transmitted second ultrasonic pulse, respectively, and
the variable n refers to a particular sample in time.

It should be noted that modern analog to digital converters might not require the sample and hold circuits. Also, it should be noted that the digital in-phase and digital quadrature representative signals can be generated directly from a digital representation of the original signal prior to entering the analog mixers. This would obviate the need for these mixer components.

The FIG. 2 apparatus for indicating mechanical stiffness properties of body tissue, constructed in accordance with the present invention, further includes indicating means responsive to the first signal representative of the position of the target after deformation of the target caused by the transmitted first ultrasonic pulse and the second signal representative of the position of the target after deformation of the target caused by the transmitted second ultrasonic pulse for indicating the change of deformation of the target caused by the transmitted second ultrasonic pulse relative to the deformation of the target caused by the transmitted first ultrasonic pulse. For the FIG. 2 embodiment of the present invention, such indicating means include means for determining the phase of the first signal representative of the position of the target after deformation of the target by the transmitted first ultrasonic pulse relative to a reference and the phase of the second signal representative of the position of the target after deformation of the target by the transmitted second ultrasonic pulse relative to the same reference. The FIG. 2 embodiment of the present invention may be characterized as the phase difference embodiment.

In particular, for the FIG. 2 embodiment of the present invention, it can be shown that the phase difference, at any given instant in time, between the waveform of the first signal representative of the position of the target after deformation of the target by the transmitted first ultrasonic pulse and the waveform of the second signal representative of the position of the target after deformation of the target by the transmitted second ultrasonic pulse is given by:

$$\Delta = arctan([I_1(n)Q_2(n) - Q_1(n)I_2(n)]/[I_1(n)I_2(n) + Q_1(n)Q_2(n)])$$

where
$\Delta$ represents the phase difference, and
the remaining terms represent the in-phase and quadrature signal components Because this phase difference is a fraction of the wavelength of the mixer reference signal ($f_o$), the displacement in distance is determined as follows:

$$Displacement = \Delta C/2\pi f_o$$

where C is the velocity of sound in the medium

In the FIG. 2 embodiment of the present invention, an estimator 54 develops a signal representative of the phase difference between the first signal representative of the position of the target after deformation of the target by the transmitted first ultrasonic pulse and the second signal representative of the position of the target after deformation of the target by the transmitted second ultrasonic pulse to drive a display 56 to present the image of the target and the deformation of the target. Specifically, estimator 54 determines the phase difference $\Delta$ and multiplies the phase difference $\Delta$ by the ratio of C divided by $2\pi$ times the mixer reference signal frequency ($f_o$). It should noted that the gain of the digital signals representative of the reflections is adjusted to compensate for the differences in the acoustic intensities of the transmitted ultrasonic pulses prior to performing the phase difference estimate operation.

Again, it should be noted that the signal developed by estimator 54, that is representative of the phase difference between the first signal representative of the position of the target after deformation of the target by the transmitted first ultrasonic pulse and the second signal representative of the position of the target after deformation of the target by the transmitted second ultrasonic pulse, also can drive a meter that indicates, in either analog or digital form, the deformation of the target.

Although illustrated and described above with reference to certain specific embodiments, the present invention nevertheless is not intended to be limited to the details shown. Rather, various modifications may be made in the details within the scope and range of equivalents of the claims and without departing from the spirit of the invention.

What is claimed:

1. Apparatus for indicating mechanical stiffness properties of body tissue, said apparatus comprising:
   transmitter means for transmitting to a target in a body:
   (a) a first ultrasonic pulse having a first acoustic intensity sufficient to deform the target, and
   (b) subsequently a second ultrasonic pulse having a second acoustic intensity, different from the acoustic intensity of the transmitted first ultrasonic pulse, sufficient to deform the target;
   receiver means for receiving:
   (a) a reflection from the target of the transmitted first ultrasonic pulse and developing a first signal representative of the position after deformation of the target caused by the transmitted first ultrasonic pulse, and
   (b) subsequently a reflection from the target of the transmitted second ultrasonic pulse and developing a second signal representative of the position after deformation of the target caused by the transmitted second ultrasonic pulse; and
   indicating means responsive to the first signal and the second signal for indicating the change of deformation of the target caused by the transmitted second ultrasonic pulse relative to the deformation of the target caused by the transmitted first ultrasonic pulse.

2. Apparatus for indicating mechanical stiffness properties of body tissue according to claim 1 wherein said indicating means include a display that presents an image of the target and the deformation of the target.

3. Apparatus for indicating mechanical stiffness properties of body tissue according to claim 2 wherein said indicating means include:

(a) means for shifting a selected segment of the waveform of one of the first signal and the second signal relative to the same segment of the waveform of the other signal till maximum coincidence of the selected segments of the waveforms is achieved, and (b) means for developing a signal representative of the relative shift in the selected segments of the waveforms to achieve maximum coincidence of the selected segments of the waveforms to drive said display to present the image of the target and the deformation of the target.

4. Apparatus for indicating mechanical stiffness properties of body tissue according to claim 2 wherein said indicating means include:

(a) means for determining the phase of the first signal relative to a reference and the phase of the second signal relative to the same reference, and (b) means for developing a signal representative of the phase difference between the first signal and the second signal to drive said display to present the image of the target and the deformation of the target.

5. A method for indicating mechanical stiffness properties of body tissue, said method comprising the steps of:

transmitting to a target in a body a first ultrasonic pulse having a first acoustic intensity sufficient to deform the target;

receiving a first reflection from the target of the transmitted first ultrasonic pulse;

transmitting a second ultrasonic pulse having a second acoustic intensity, different from the acoustic intensity of the transmitted first ultrasonic pulse, sufficient to deform the target;

receiving a second reflection from the target of the transmitted second ultrasonic pulse;

developing from the first reflection a first indication of deformation of the target caused by the transmitted first ultrasonic pulse;

developing from the second reflection a second indication of deformation of the target caused by the transmitted second ultrasonic pulse; and developing from the first deformation indication and the second deformation indication an indication of the deformation of the target caused by the transmitted second ultrasonic pulse relative to the deformation of the target caused by the transmitted first ultrasonic pulse.

6. A method for indicating mechanical stiffness properties of body tissue according to claim 5 wherein the step of developing an indication of the deformation of the target caused by the transmitted second ultrasonic pulse relative to the deformation of the target caused by the transmitted first ultrasonic pulse includes:

(a) shifting a selected segment of the waveform of one of the reflection of the transmitted first ultrasonic pulse and the reflection of the transmitted second ultrasonic pulse relative to the same segment of the waveform of the reflection of the other transmitted ultrasonic pulse till maximum coincidence of the selected segments of the waveforms is achieved, and (b) developing an indication of the relative shift in the selected segments of the waveforms to achieve maximum coincidence of the selected segments of the waveforms.

7. A method for indicating mechanical stiffness properties of body tissue according to claim 5 wherein the step of developing an indication of the deformation of the target caused by the transmitted second ultrasonic pulse relative to the deformation of the target caused by the transmitted first ultrasonic pulse includes:

(a) determining the phase of the reflection of the transmitted first ultrasonic pulse relative to a reference and the phase of the reflection of the second ultrasonic pulse relative to the same reference, and (b) developing an indication of the phase difference between the reflection of the transmitted first ultrasonic pulse and the reflection of the transmitted second ultrasonic pulse.

* * * * *